United States Patent [19]

Lamond et al.

[11] Patent Number: 5,139,474
[45] Date of Patent: Aug. 18, 1992

[54] MEDICAL TREATMENT DEVICE WITH SELF-CENTERING SECURING MEMBERS

[75] Inventors: Donald R. Lamond, Lynbrook, N.Y.; Bert Heinzelman, Tenafly, N.J.

[73] Assignee: IatroMed, Inc., Phoenix, Ariz.

[21] Appl. No.: 600,416

[22] Filed: Oct. 19, 1990

[51] Int. Cl.$^5$ .............................................. A61N 1/00
[52] U.S. Cl. ..................................... 600/15; 128/802; 128/419 F
[58] Field of Search ................. 600/9, 15; 128/419 F, 128/802; 269/322, 324, 325

[56] References Cited

U.S. PATENT DOCUMENTS

| 2,404,283 | 7/1946 | Gieringer | 128/802 |
| 4,266,532 | 5/1981 | Ryaby et al. | |
| 4,456,001 | 6/1984 | Pescatore | |
| 4,550,714 | 11/1985 | Talish et al. | |
| 4,616,629 | 10/1986 | Moore | |
| 4,635,643 | 1/1987 | Brown | |
| 4,932,951 | 6/1990 | Liboff et al. | 600/15 |

Primary Examiner—William E. Kamm
Assistant Examiner—J. P. Lacyk
Attorney, Agent, or Firm—Dykema Gossett

[57] ABSTRACT

A medical treatment device is disclosed which includes a medical treatment member and resilient securing members which adjust to conform to the particular dimensions of the portion of the patient's anatomy which is to be treated. The resilient securing members move outwardly away from the patient to conform to the size of the patient and ensure that the patient is centered within the treatment device. The medical treatment members are thus accurately positioned with respect to the patient. This is particularly important in treatments involving the application of magnetic fields to the patient. In addition, the disclosed medical device is relatively comfortable and can be worn by a patient for a relatively long period of time.

10 Claims, 2 Drawing Sheets

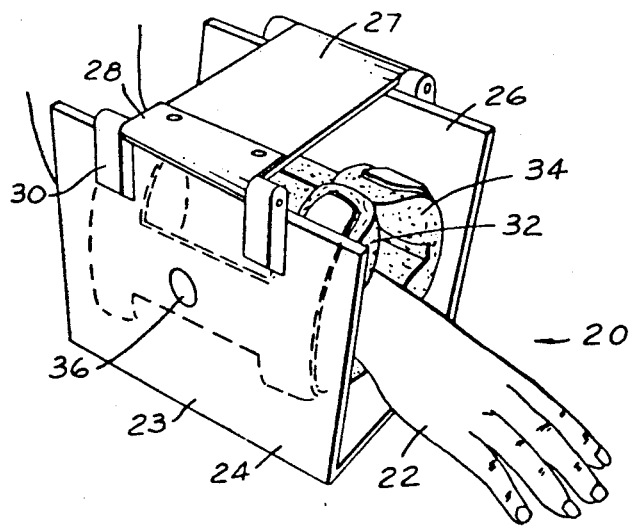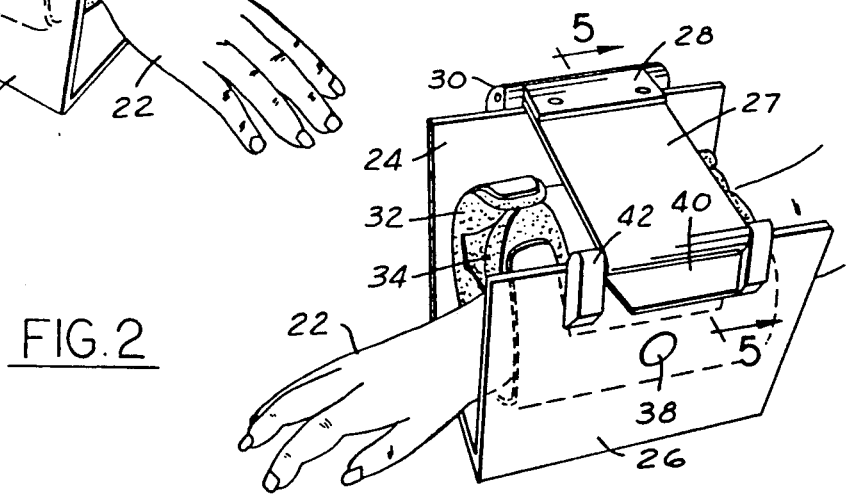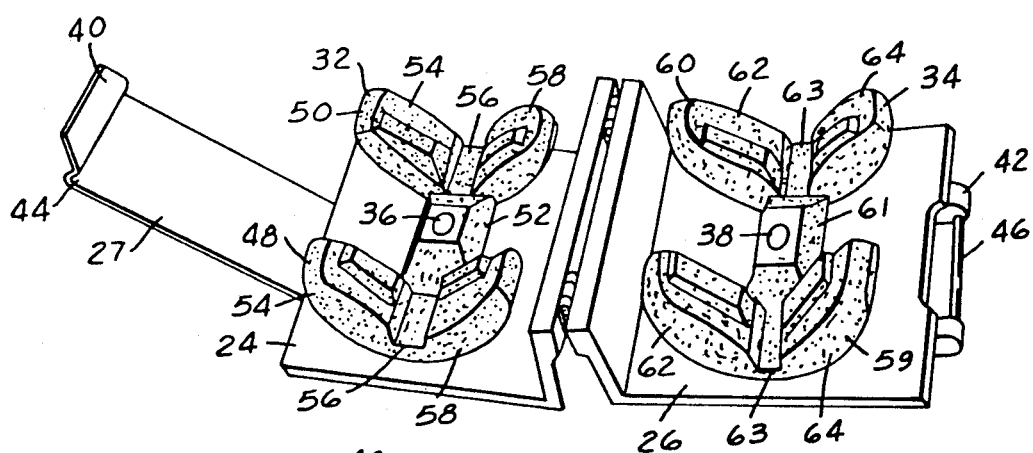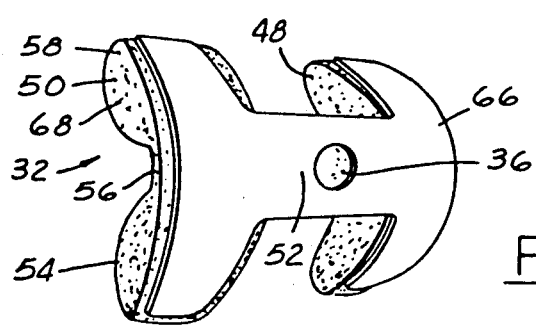

MEDICAL TREATMENT DEVICE WITH SELF-CENTERING SECURING MEMBERS

BACKGROUND OF THE INVENTION

This invention relates to a medical treatment device for treating a patient. More particularly, this invention relates to a securing means for a treatment member which adapts itself for use with a wide variety of individual patients and body parts of a particular patient.

Several medical treatment devices are known which are secured to a patient to apply medical treatment for a period of time. As an example, magnetic treatment devices are known which apply a magnetic field to a particular portion of a patient to provide a number of therapeutic benefits. These treatment devices have enjoyed success over the past years, however, some problems still exist in terms of the patient-interface assembly.

A major problem is mounting the devices such that they can be used with the wide variety of anatomical geometrics that the device will encounter. To be economically feasible, the device must be utilized with a large cross-section of patients. It is not always practical to tailor a device to an individual patient, and thus, to be practical, the device must adjust to the size of the patient.

This also increases the difficulty of properly positioning the treatment members with respect to a patient which is important in many such devices. As an example, in the application of a magnetic field to a patient it is generally important that the medical treatment member, or the field generating means, be accurately and precisely positioned relative to a particular portion of the patient's anatomy to attain optimum therapeutic results. With the prior art devices, it is difficult to accurately and reproducibly position the medical treatment device.

Further problems exist in that most devices for securing medical treatment devices to a patient used in the prior art are somewhat uncomfortable. This is burdensome to the patient, since these devices are often worn for relatively long periods of time.

It is known in the prior art to mount medical treatment members in a deformable material such that they can be shaped to an individual patient. The clay-like materials typically utilized are somewhat adaptable to a particular patient; however, they do not totally address the problem of properly positioning a medical treatment member with respect to the patient. By deforming the material, the position or shape of the medical treatment member may sometimes be moved. For this reason, it may be difficult to accurately position the device. In addition, such deformable materials do not fully address the discomfort problem. These deformable members typically require a relatively great amount of deformable material to adequately adjust to the size of a particular patient. For this reason, they are relatively heavy and uncomfortable.

It is therefore an object of the present invention to provide a securing means for a medical treatment member that adapts itself to various sizes of patients. In addition, it is an object of the present invention to provide such a device in which the securing means allows a patient to comfortably wear the device for a relatively long period of time.

SUMMARY OF THE INVENTION

The present invention discloses a medical treatment device, or anatomical interface device, which comprises a treatment member mounted a first radial distance from an approximate center of the device when in a treatment position. A resilient securing means is positioned radially inwardly from the treatment member and secures the device on a patient. The resilient securing means moves radially outwardly to conform to the shape of an individual patient such that the treatment member maintains its position, and is properly positioned with respect to a particular patient. In a disclosed embodiment, the resilient securing means is formed of a resilient foam that deforms outwardly to conform to the individual patient while maintaining accurate positionong of the medical treatment member.

The disclosed device adapts to a wide variety of anatomical sizes, profiles and contours of the particular treatment area, and to the anatomies of most patients. The securing members have a relatively small contact area, even-grip pressure, and are preferably formed of a soft low-density foam such that they are quite comfortable, and do not create pressure points, even during extended periods of treatment. The resilient securing device ensures consistent and accurate positioning of the treatment member, and is self-centering and self-adjusting to maintain accurate positioning.

One disclosed embodiment is constructed such that it becomes stiffer in a direction moving radially outwardly from the center of the device. This variable stiffness ensures even and constant pressure. Further, the resilient foam may vary in density across its radial dimension such that it becomes denser at its radially outermost portion.

In a preferred embodiment of the present invention, the resilient securing means comprises two opposed resilient securing, or interface members spaced radially about an approximate center of the device. The opposed portions of the members each preferably defines three-parts, with a first center part being parallel to a center part of the opposed resilient member and second and third parts, or fingers, extending at an angle to the center part, such that each resilient securing member is generally V-shaped in cross-section. Most preferably, each resilient securing member has two V-shaped portions with a central interconnecting portion positioned radially outwardly from the V-shaped portion, and receiving the medical treatment member.

The use of the two spaced portions ensure that a conically-shaped body member, such as a leg, will also be adequately gripped. In a device that has only a single portion, the relatively larger part of the conically-shaped body member, as an example the upper part of the leg, would sometimes not be adequately gripped and the medical treatment device could move on the patient. The use of the two separate portions ensures adequate gripping on both the relatively larger and relatively smaller parts of a conically-shaped body portion.

The securing member preferably has a flexible plastic backing at the radially outermost surface. As the resilient securing members deformed to conform to the shape of a particular patient, the resilient securing members flex and apply a force tending to flex the flexible plastic backing. The flexible plastic backing applies a reaction spring force radially inwardly, which ensures that the device is secured to a patient. In a most preferred embodiment of the present invention, the foam securing members extend over a smaller surface area at a radially inward position, than they do at radially outward positions. Due to this feature, it is ensured that the foam will easily deform when the device is used on a smaller patient, such that the foam deforms sufficiently that the flexible plastic backing is flexed.

In a most preferred embodiment of the present invention, a rigid yoke is formed from shells disposed radially outwardly of each resilient securing member. The two shells are preferably hinged to each other to form the yoke and are pivotable away from each other to a non-treatment position and towards each other to a treatment position. A latch secures the rigid shells at the treatment position.

The medical treatment device is preferably positioned over an area of a patient to be treated, such as a limb, and are pivoted into the treatment position. As the two resilient securing members contact the patient's limb, they flex and deform outwardly to adjust to the exact contour and size of the individual patient. The resilient securing means ensures that they patient's limb will be comfortably centered within the device, and that the medical treatment member will be properly positioned with respect to the patient.

These and other objects and features of the present invention can be best understood from the following specification and drawings, of which the following is a brief description.

BRIEF DESCRIPTION OF THE DRAWINGS

FIG. 1 is a perspective view of a first side of a medical treatment device according to the present invention.

FIG. 2 is a perspective view of the opposite side of the treatment device illustrated in FIG. 1.

FIG. 3 is a perspective view of the medical treatment device illustrated in FIGS. 1 and 2 in a non-treatment position.

FIG. 4 is a perspective view of a resilient securing means.

BRIEF DESCRIPTION OF THE PREFERRED EMBODIMENT

Figure 5:
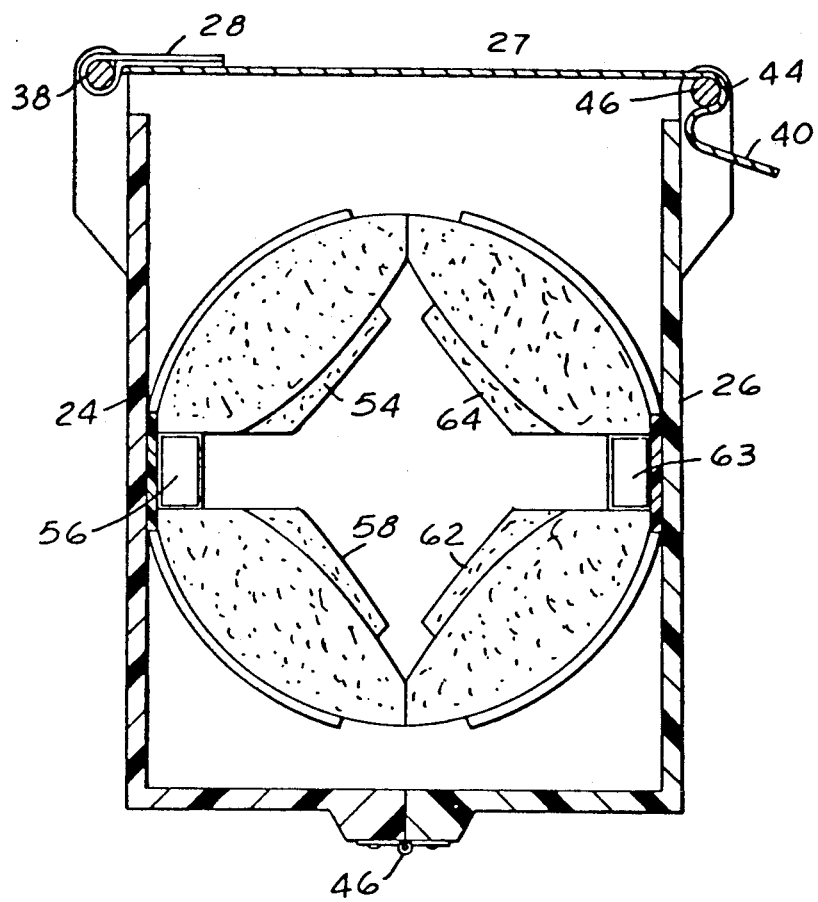
FIG. 5 is a cross-sectional view along line 5—5 as shown in FIG. 2.

A disclosed embodiment of the present invention can be best understood with reference to FIGS. 1 through 5. As shown in FIG. 1, medical treatment device 20 is mounted on patient 22, and includes a hinged yoke 23 formed of first shell half 24 and second shell half 26. Shells 24 and 26 are preferably formed of rigid plastic material to protect the internal portions of medical treatment device 20. Latch 27 is pivotally attached through latch hinge 28 to mount 30 of first shell half 24. Latch 27 secures first and second shell halves 24 and 26 in the treatment position illustrated in FIGS. 1 and 2.

First securing or interface member 32 is mounted on one side of the approximate center of medical device 20, and second securing member 34 is mounted on the opposed side. Medical treatment device 36 is disposed in a center of first shell half 24 and extends through first securing member 32 such that an inwardly facing treatment face applies treatment to patient 22. Medical treatment device 36 can be any device which applies a treatment to a patient. The exact structural details of how medical treatment device 36 is mounted to shell 24 forms no part of this invention.

FIG. 2 shows the opposed side of medical device 20, which may include a second medical treatment member 38 mounted in second shell half 26. Latch clip 40 is received on latch mount 42 to secure first and second shell halves 24 and 26 in the treatment position.

Medical treatment device 20 is illustrated in an non-treatment position in FIG. 3. Catch 44 of latch clip 40 may be received on bar 46 of latch mount 42 to secure shell halves 24 and 26 in the treatment position. The details of securing members 32 and 34 can be understood from this non-treatment position. First V-shaped member 48 is formed at one end of first securing member 32 and second V-shaped member 50 is at the other end. First and second V-shaped members 48 and 50 are interconnected by interconnecting member 52 such that securing member 32 is generally I-shaped when viewed from a center of medical treatment device 20. Each V-shaped member 48 and 50 includes finger or side member 54, central member 56 and opposed finger or side member 58. Second securing member 34 has V-shaped members 59 and 60 and interconnecting member 61. V-shaped members 59 and 60 include side 62, center member 63 and opposed side 64. Interconnecting members 52 and 61 are shown receiving treatment members 36 and 38, respectively.

FIG. 4 illustrates first securing member 32 including V-shaped member 50 having side portions 54 and 58, and central member 56. Flexible plastic backing 66 mounts foam material 68 which defines the actual surface of the V-shaped members 48 and 50. Preferably, a polyurethane foam is utilized for foam portions 68.

It is also envisioned that the density of foam portion 68 may vary across its radial extent and become denser moving in a radially outward direction. This would ensure constant and even pressure from the V-shaped members on a patient. The entire device could be said to become stiffer as one moves radially outwardly from foam portion 68 to backing material 66 and to yoke 23 which is radially outward of backing 66. This increasing stiffness ensures constant and even-grip pressure, providing greater patient comfort.

The self-centering features of treatment device 20 will be explained with reference to FIG. 5. When medical treatment device 20 is in a treatment position, opposed sides 54 and 58 of first shell 24, and 62 and 64 of second shell 26 are spaced about the approximate center of treatment device 20. Since each sides 54, 58, 62, and 64 is resilient, they deform radially outwardly to adjust to the particular size of a patient when the treatment device is moved to this treatment position. It is preferable that the resilient sides extend inwardly to such an extent that they are deformed by the smallest size patient upon whom treatment device 20 will be utilized. It may be preferable to have a plurality of sizes of treatment devices to conform to differing limbs, or body sizes of patients. As an example, it may be preferable to have extra large, large, medium and small devices. Further, it may be preferable to have separate leg and arm devices.

When medical treatment device 20 is positioned about a patient and moved to the treatment position, the patient's body shape deforms sides 54, 58, 62 and 64 radially outwardly to center the device about the patient. Latch 40 is then snapped over latch clip 44 to secure first and second shells 24 and 26 in the treatment position. The treatment members 36 and 38 are thus properly positioned with respect to the patient.

As sides 54, 58, 62 and 64 deform or flex radially outwardly, they tend flex flexible plastic backing 66. As flexible plastic backing 66 flexes, a resultant spring force is applied radially inwardly to secure the device to a patient. Thus, flexible plastic backing members 66 act as springs to ensure that securing members 32 and 34 secure the device to the patient, even when the area of the patient to be treated is relatively small.

Further, the use of two separate V-shaped members 48 and 50 ensures that the device will be adequately secured on a conically-shaped body portion such as a limb. Each V-shaped portion 48 and 50 deforms independently of the other to conform to the exact size of the conically-shaped body portion. One V-shaped portion conforms to a relatively larger body part and the other conforms to the relatively smaller body part of a conically-shaped body portion, such as a leg.

In a most preferred embodiment, it is envisioned that medical treatment members 36 and 38 will be a magnetic treatment assembly such as is disclosed in U.S. Pat. No. 4,932,951. Such a device utilizes a pair of opposed Helmholtz coils to apply a predetermined field to an area of the patient. The self-centering feature of the present invention allows the patient treatment site to be centered within device 20 so that the coils are positioned with respect to the patient for best therapeutic results.

Figure 6:
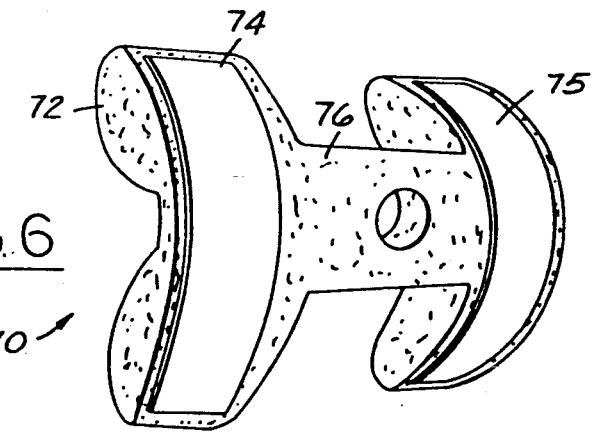
FIG. 6 is a perspective view of a second embodiment of the resilient securing means.

A second embodiment 70 of the resilient securing member is illustrated in FIG. 6. This embodiment includes foam portion 72 having two separate flexible plastic backings 74 and 75 spaced about center 76.

Alternatively, the backing may be one-piece, and the foam formed of three separate pieces.

Figure 7:
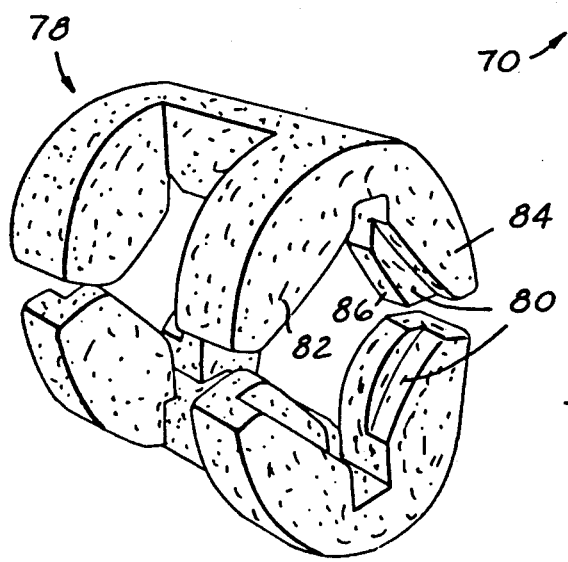
FIG. 7 is a perspective view of a third embodiment of the resilient securing member.

A most preferred embodiment of a resilient securing member 78 according to the present invention is shown in FIG. 7. Foam member 78 has notches 80 in sides 82 and 84 at its axially outermost ends. The remaining portions 86 are formed at the radially innermost portions of foam members 78, and contact the patient over a relatively small surface area. Due to the relatively small amount of foam on portions 86, portions 86 flex radially outwardly easily and ensure that flexible plastic backings 66 will be flexed and that a spring force will be applied radially inwardly into foam member 78. In a sense, foam member 78 acts as a two parts spring. As a patient's anatomy causes foam member 78 to deform through portion 86, the force required to deform foam member 78 is relatively small. Once the foam member 78 has been deformed through portion 86, that is through the extent of notch 80, foam member 78 contacts the patient over its entire axially length. At this point, it becomes more difficult to deform foam member 78 and to also flex flexible plastic backing 66. The relatively easy to deform portion 86 ensures that when the device issues with a portion of a patient having a relatively small diameter, the foam member 78 will deform sufficiently, such that flexible plastic backing 66 is deformed to cause a spring force radially inwardly to secure the advice to the patient. Alternatively, a chamfer could replace notch 80.

Most preferably, the resilient securing members are formed by pre-spraying a mold with an elastomeric urethane coating and then injecting a foam into the mold. The resulting securing member will have a coating at the outside, with a urethane foam at an interior surface. Flexible plastic backing 66, or 74 and 75, are then affixed to the device.

Other means of making the resilient securing means are also envisioned, including envelope molding. With this process, a fabric is laid into a mold and a foam is inserted under pressure to push the fabric against the mold, bonding it, and forming a permanent fabric cover. It is also possible to use a plain urethane foam without a coating as described above. It should be understood that the features of this invention extend to any type of resilient member which adjusts to a patient to ensure that the medical treatment member is accurately positioned.

In preferred embodiments, the foam is a polyurethane foam, and most preferably foam available under the tradename Bayfit TM from Mobay Corporation in Pittsburg, Pa. The coating, or skin material is most preferably a latex or polyurethane prespray. The shell, or yoke, is formed of a rigid plastic, most preferably a polycarbonate structured foam available under the tradename Lexan TM Structured Foam from General Electric Company in Pittsfield, Mass. The backing is preferably formed from an acrylic/polyvinylchloride, most preferably available under the tradename Kydex 100 TM from Kleerdex Company in Bloomsburg, Pa.

In addition, although the medical treatment device is disclosed for use with magnetic treatment members, it could also be used for braces, splints, vital sign monitoring devices such as blood pressure monitoring or radiographic positioning. Further, the above list is only exemplary and not all inclusive.

Preferred embodiments of the present invention have been disclosed, however, a worker of ordinary skill in the art would realize that certain modifications could be made to the disclosed embodiments of this invention and still come within the scope of this invention, for this reason the scope of the following claims should be studied in order to determine the true scope and content of the present invention.

We claim:

1. A medical treatment device comprising:
   a magnetic treatment member for treating a patient, said treatment member being mounted a first radial distance from an approximate center of the device when in a treatment position;
   a relatively rigid shell, said magnetic treatment member being mounted to said rigid shell, said rigid shell comprising two rigid halves which are hinged together at a single hinge axis, said two shell halves being pivotable away from each other to a nontreating position, and pivoting towards each other to said treatment position;
   means for securing said shell halves together at said treatment position with said first radial distance being relatively fixed and predictable; and
   relatively resilient securing members extending radially inwardly from said shall halves and being deformable radially outwardly to conform to the shape of an individual patient, said first radial distance remaining relatively constant as said resilient securing members deform radially outwardly.

2. A medical treatment device as recited in claim 1, wherein said means for securing includes a latch which retains said shell halves together at said treatment position.

3. A medical treatment device as recited in claim 1, wherein said resilient securing means comprises two opposed resilient members spaced radially about an approximate center of the device.

4. A medical treatment device as recited in claim 3, wherein each of said opposed resilient securing members comprises a three-part shape with a center part disposed parallel to a center part of the opposed securing member, and the second and third parts of said resilient securing members extending at an angle to said center part such that each said resilient securing member is generally V-shaped in cross-section.

5. A medical treatment device as recited in claim 4, wherein each of said resilient securing members are formed of a foam.

6. A medical treatment device as recited in claim 5, wherein each of said resilient securing members comprises two V-shaped portions spaced along a central axis of the device and a portion interconnecting said two V-shaped portions, with said interconnecting portion being disposed radially outwardly from said V-shaped portions.

7. A medical treatment device as recited in claim 6, wherein said treatment member is received on said interconnecting portion.

8. A medical treatment device comprising:
   a treatment member for treating a patient, said treatment member being mounted a first radial distance from an approximate center of the device when in a treatment position;
   two opposed resilient securing members formed of a foam, and positioned radially inwardly from said treatment member and securing said treatment member on a patient, said resilient securing members moving radially outwardly to conform to the shape of an individual patient;
   each of said opposed resilient securing members comprises a three-part shape with a center part disposed parallel to a center part of the opposed securing member, the second and third parts of said resilient securing members extending at an angle to said center part such that each said resilient securing member is generally V-shaped in cross-section; and
   rigid shells disposed radially outwardly of each said resilient securing member, said shells being hinged to each other and pivotable away from each other to a non-treating position, and towards each other to the treatment position.

9. A medical treatment device as recited in claim 8, wherein each of said resilient securing members comprises two V-shaped portions spaced along a central axis of the device and a portion interconnecting said two V-shaped portions, with said interconnecting portion being disposed radially outwardly from said V-shaped portions.

10. A medical treatment device as recited in claim 8, wherein a latch secures said rigid shell portions at the treatment position.

* * * * *

UNITED STATES PATENT AND TRADEMARK OFFICE
CERTIFICATE OF CORRECTION

PATENT NO. :   5,139,474
DATED       :   August 18, 1992
INVENTOR(S) :   Lamond, et al.

It is certified that error appears in the above-identified patent and that said Letters Patent is hereby corrected as shown below:

In col. 6, line 56, "shall" should read "shell"

Signed and Sealed this

Fourth Day of January, 1994

Attest:

BRUCE LEHMAN

*Attesting Officer*     *Commissioner of Patents and Trademarks*